US011275055B2

(12) United States Patent
Michaelis (10) Patent No.: US 11,275,055 B2
(45) Date of Patent: Mar. 15, 2022

(54) DETONATION PICKUP TESTER AND METHODOLOGY

(71) Applicant: Chad Alan Michaelis, Aledo, TX (US)

(72) Inventor: Chad Alan Michaelis, Aledo, TX (US)

(73) Assignee: OMNI IP LLC, Cresson, TX (US)

( * ) Notice: Subject to any disclaimer, the term of this patent is extended or adjusted under 35 U.S.C. 154(b) by 64 days.

(21) Appl. No.: 16/652,975

(22) PCT Filed: Oct. 2, 2018

(86) PCT No.: PCT/US2018/053943
§ 371 (c)(1),
(2) Date: Apr. 1, 2020

(87) PCT Pub. No.: WO2019/070690
PCT Pub. Date: Apr. 11, 2019

(65) Prior Publication Data
US 2020/0326307 A1    Oct. 15, 2020

Related U.S. Application Data

(60) Provisional application No. 62/566,621, filed on Oct. 2, 2017.

(51) Int. Cl.
*G01N 27/72* (2006.01)
*G01N 27/04* (2006.01)
*G01N 33/28* (2006.01)

(52) U.S. Cl.
CPC ............ *G01N 27/72* (2013.01); *G01N 27/04* (2013.01); *G01N 33/2817* (2013.01); *G01N 33/2829* (2013.01)

(58) Field of Classification Search
CPC .... G01N 27/72; G01N 27/04; G01N 33/2817; G01N 33/2829
See application file for complete search history.

(56) References Cited

U.S. PATENT DOCUMENTS

| | | | | |
|---|---|---|---|---|
| 2,619,605 A | * | 11/1952 | Lancor, Jr. | G01L 23/22 310/26 |
| 5,495,757 A | * | 3/1996 | Atanasyan | F02B 77/085 324/380 |
| 2015/0120211 A1 | * | 4/2015 | Michaelis | G01N 33/22 702/22 |

* cited by examiner

*Primary Examiner* — Jermele M Hollington
*Assistant Examiner* — Taqi R Nasir
(74) *Attorney, Agent, or Firm* — Carrington, Coleman, Sloman & Blumenthal, L.L.P.

(57) ABSTRACT

A detonation pickup testing system, comprising: (i) apparatus for coupling to at least one terminal of a detonation pickup; and (ii) a computational system, for communicating with the pickup via with the apparatus, to test at least one characteristic, excluding or in addition to DC resistance, of the detonation pickup.

23 Claims, 10 Drawing Sheets

DETONATION PICKUP TESTER AND METHODOLOGY

TECHNICAL FIELD

The preferred embodiments relate to testing detonation or combustion pickups for measuring octane or cetane.

BACKGROUND ART

The processes of measuring fuel octane or cetane, such as those prescribed in several ASTM standards, require the use of a detonation or combustion pickup (later referred to as combined term detonation pickup) connected to a test engine. The test engine is run, and in response the detonation pickup connected to the test engine produces an electrical signal representing one or more combustion characteristics of the test engine. The detonation pickup typically is used to sense pressure or vibration resulting from changes within the combustion chamber of the test engine.

A typical detonation pickup is exposed to elevated temperatures and vibration that may result in detonation pickup degradation or failure. Inaccuracy in a detonation pickup can be a considerable cost to the process of blending fuels to an exact level, which itself is an expensive process. Specifically, the detonation pickup is at the fuel testing signal chain's heart, and there are many costs associated with a low or inaccurately performing detonation pickup. One detonation pickup's inferior performance can be a large cost driver in the fuel blending process. These costs can be greatly compounded over a testing fleet. An erroneous signal or failure of the detonation pickup may be costly to troubleshoot or to correct an incorrectly measured value.

Often in the prior art, after some period of use, it has been an industry standard to measure only the DC resistance of a detonation pickup to determine its health or its fitness for ongoing use in the process of determining an octane number. Thus, based solely on changes in an occasional DC resistance measure (i.e., testing) of the detonation pickup, a sensor is discarded, or sent out for refurbishment, so as to avoid potential erroneous measure from a potentially degraded or otherwise vulnerable sensor. The present inventor has recognized that the drawbacks of such an approach and, the preferred embodiments, therefore, seek to improve upon the prior art. Such preferred embodiments are further explored below.

DISCLOSURE OF INVENTION

In one preferred embodiment, there is a detonation pickup testing system. The system comprises: (i) apparatus for coupling to at least one terminal of a detonation pickup; and (ii) a computational system, for communicating with the pickup via with the apparatus, to test at least one characteristic, excluding or in addition to DC resistance, of the detonation pickup.

In another preferred embodiment, there are apparatus used to test a detonation pickup, the detonation pickup for testing ignition properties of fuel. the apparatus comprise: (i) a member for coupling to the pickup; and apparatus, coupled to the member, for retaining a movable device relative to the member, the apparatus for retaining comprising apparatus for retaining the movable member at a first position away from a face of the pickup and apparatus for releasing the apparatus for retaining so as to apply an increase in force against the face.

Other aspects are also described and claimed.

DESCRIPTION OF EMBODIMENTS

According to certain preferred embodiments, apparatus and methodology are provided for evaluating a detonation pickup by causing, storing, and analyzing pickup attributes by: (i) applying a force to the face of a detonation pickup sensor; and/or (ii) applying electrical energy to the pickup's electrical terminals, where in either case preferred embodiments record attributes and characteristics of the detonation pickup in response to the applied force. A test apparatus receives, can record, and evaluate the response, and that tester is operable therefore, based on the force response, to describe failure or degradation of the sensor. Such aspects may be used to perform system troubleshooting, process bias detection, adjust offsets or calibration, and increase octane or cetane measurement precision. Thus, preferred embodiment tester apparatus and processes will be helpful in determining such qualities as a pickup's precision over time and health or fit-for-use.

Detonation pickups such as those described in U.S. Pat. No. 2,269,760 "Detonation Indicator" are an example of a type of detonation pickup that would benefit from the inventive scope, among others. Other types of pressure and vibration detonation pickups, used in measuring octane or cetane, also may benefit from the apparatus.

Figure 1A:
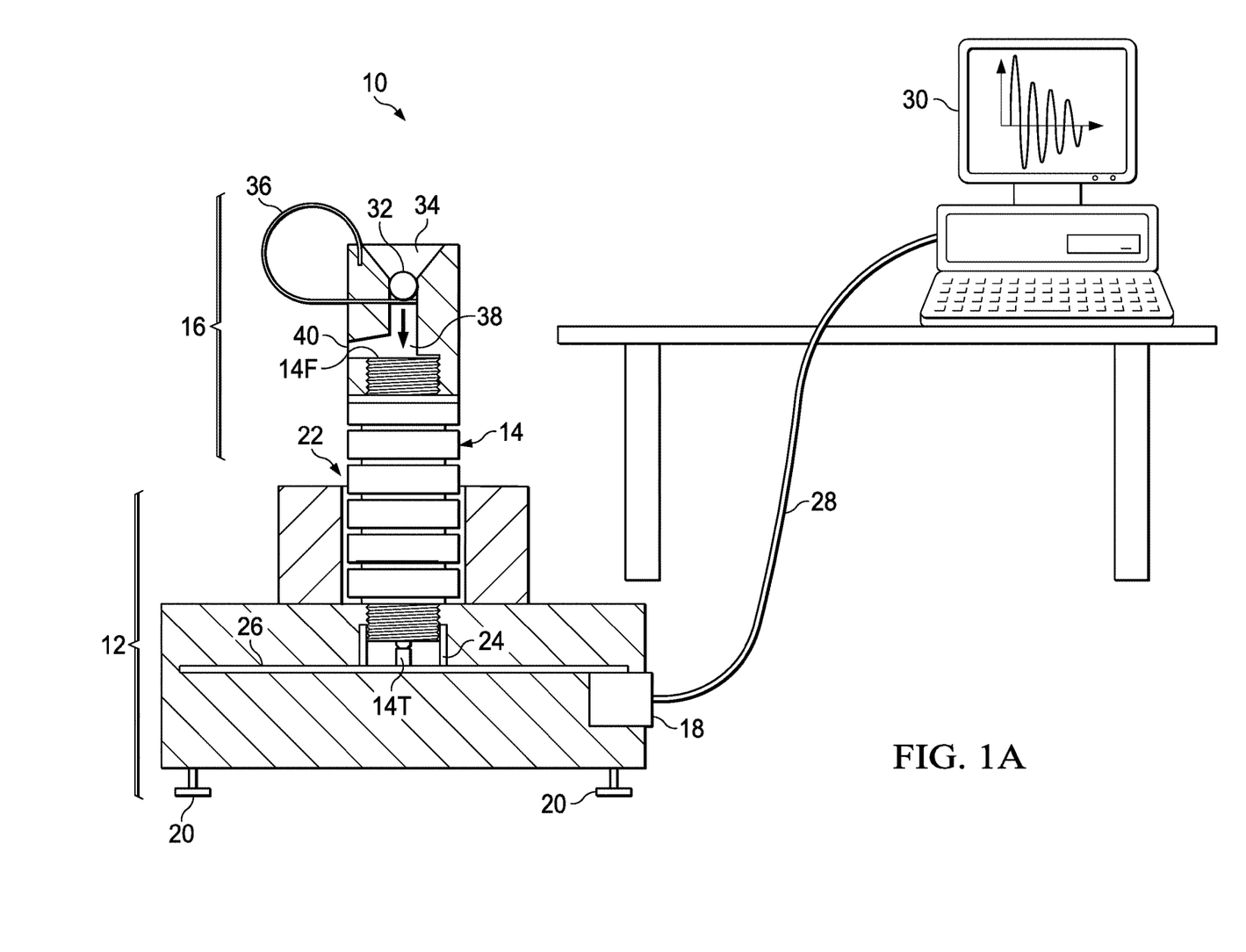
FIG. 1A illustrates a preferred embodiment detonation testing system for a detonation pickup, including an electromechanical structure for supporting the detonation pickup and controllably applying a force to a face of the detonation pickup.

FIG. 1A illustrates a preferred embodiment detonation testing system 10. System 10 includes an electromechanical structure 12 for retaining a detonation pickup 14 and also a force application member 16. In the example of FIG. 1A, the electromechanical structure 12 includes a base 18, with leveling feet 20 (e.g., screws) beneath the bottom of the base 18. The structure 12 further includes a wide aperture 22 for receiving the lower body of the pickup 14, whereupon the lowermost portion of the pickup 14, which includes electrical terminal 14T, fits within a narrow aperture 24 in the base 18. In this position, the pickup 14 is retained in a fixed position relative to the base 18, such as by a friction and/or threadable fit between the outer circumference of the pickup 14 and the inner diameter of the wide aperture 22 or likewise with the narrow aperture 24. Further, when the pickup 14 is so retained in the base 18, the terminal 14T couples (e.g., mates with, touches, or otherwise provides a conductive path) to a circuit assembly 26 that is fixed inside the base 18. The circuit assembly 26, by way of example, may be a printed circuit board (PCB) or the like, including various analog, logic, and control circuitry, for accomplishing the additional functionality described in this document.

The system 10 also includes an electrical interface 28 (e.g., cabling) for coupling a computing system 30 to the circuit assembly 26 (and indirectly, therefore, with the pickup terminals 14T), so as to provide excitation signals to the terminal 14T and/or capture attributes of an induced electrical signal response, which further occurs in response to a controlled force applied to the pickup face 14F, as further detailed below. Accordingly, the computing system 30 may comprise any of known computational devices, such as a personal computer, workstation, laptop, terminal, portable device, tablet, cell phone or the like, with sufficient computational/processing and input/output capability to achieve the functionality described herein. Further, while the electrical interface is shown as a direct electrical connection, one skilled in the art may readily modify the present teachings so as to permit wireless communication between the structure 12 and the computing system 30.

Attention is now directed to the force application member 16, which controls a mass 32, for striking the pickup face 14F. The force application member 16 is one of various preferred embodiments for controlling a mass force (e.g., by dropping the mass 32) to apply pressure to the pickup face 14F. In the FIG. 1A example of the application member 16, the falling mass 32 applies force to face 14F in response to being released from a fixed position and moving toward the face 14F by gravity. Additional details for these aspects are shown in FIG. 1A, and further in FIGS. 1B and 1C.

Figure 1B:
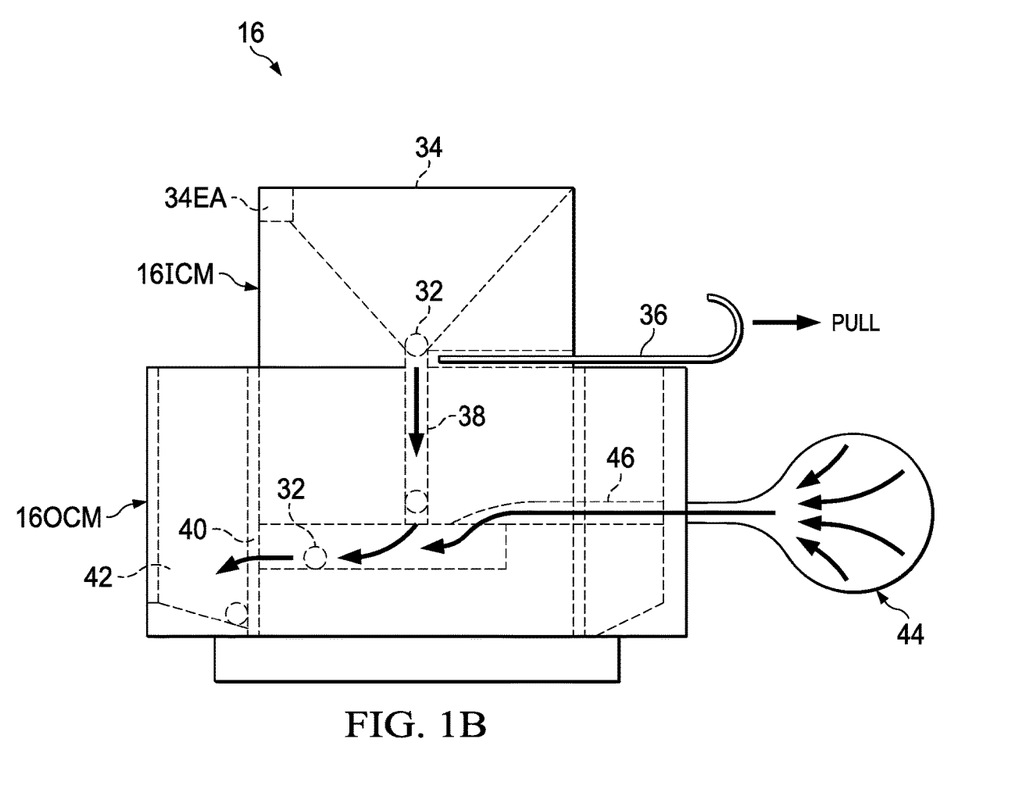
FIG. 1B illustrates additional detail of the force application member from FIG. 1A, with the falling mass in a released position so as to contact the pickup face and proceed to an exit port.
Figure 1C:
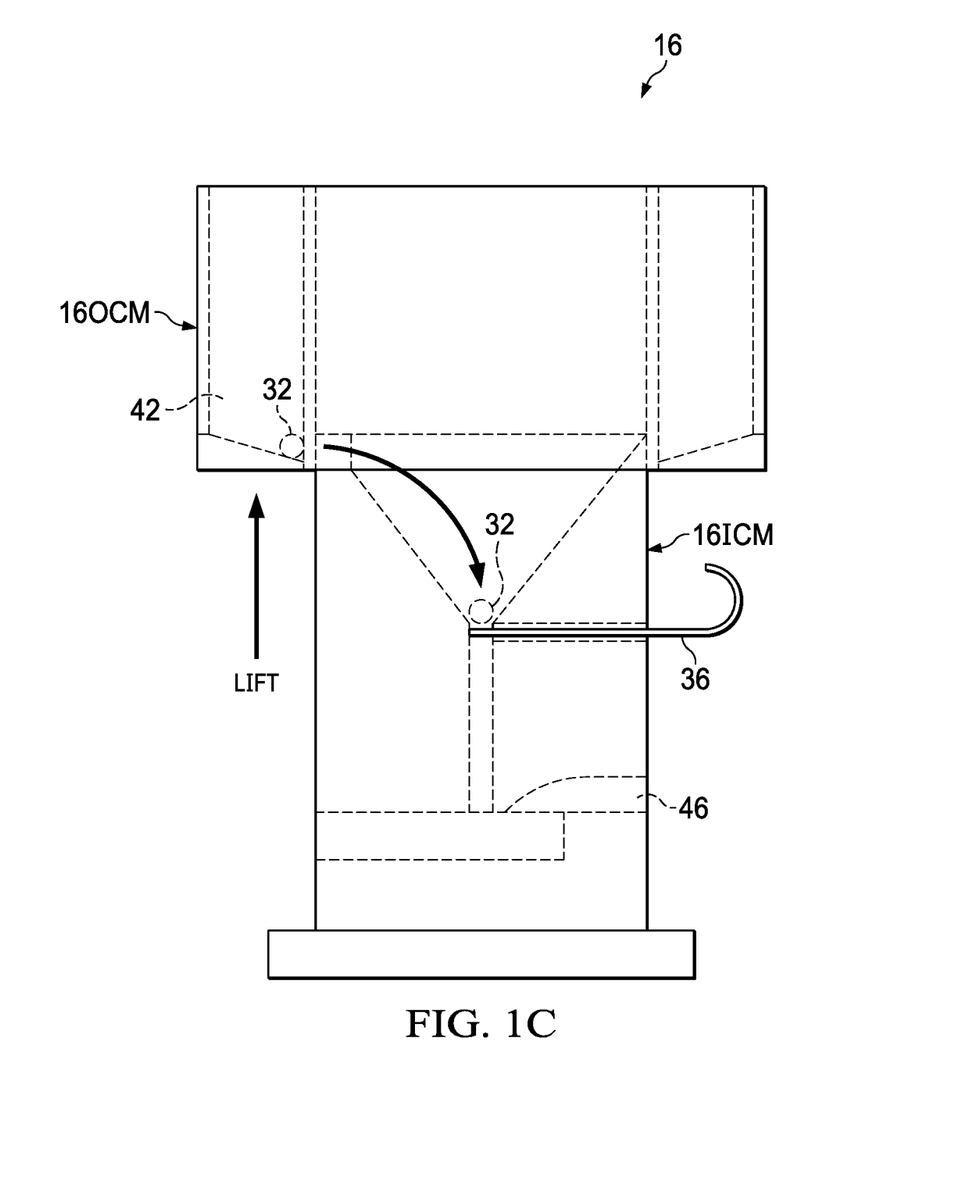
FIG. 1C illustrates additional detail of the force application member from FIG. 1A, with the falling mass in a retained position prior to being released to contact the pickup face.

The application member 16 couples to the pickup 14, such as by a threaded relationship that can screw onto the threads of the pickup that are adjacent to the pickup face 14F. The application member 16 includes an upper drop chamber 34, in which the mass 32 (e.g., a ball bearing) is initially located, atop a retaining member 36. In the example of FIGS. 1A-1C, the retaining member 36 is a spring pin (e.g., flexible metal/wire), having a lower portion that extends generally horizontally through a portion of the application member 16 and an upper portion fixed to the force application member 16, so that the retaining member 36 is not lost during or after operation. Initially, the falling mass 32 sits atop the portion of the horizontally-extending retaining member 36, in the upper drop chamber 34, which in the example of application member 16 is conical with its vertex (or apex) toward the bottom of the upper drop chamber 34, and the vertex fluidly communicates with a lower drop chamber 38. The lower drop chamber 38 may be cylindrical, so that eventually the falling mass 32 may drop from the upper drop chamber 34, through the lower drop chamber 38, to reach, and make physical contact with, the pickup face 14F.

The dropping apparatus of application member 16 are shown in additional detail in FIGS. 1B and 1C, where certain of those apparatus are not shown in FIG. 1A so as to simplify the illustration In FIG. 1B, a portion of the retaining member 36 is shown, and as shown by an arrow is pulled generally horizontally in a direction away from the member 16. As a result, the retaining member horizontal portion moves away from supporting the bottom of the mass 32, thereby allowing the mass 32 to drop from the upper chamber 34 to the lower chamber 38. While not shown in FIG. 1B, FIG. 1A illustrates the dropping direction of the mass 32 through the lower chamber 38, thereby causes the mass 32 to strike the face 14F of the pickup 14. As a result, as and further described later, the pickup 14 (assuming it is properly energized) will experience an electrical response, and that response may be detected by the circuit assembly 26 and communicated via the electrical interface 28 to the computing system 30. Hence, the operation of system 10, as thus far described, provides a controlled force application to the face 14F. Additionally, and as further appreciated below, the same (or substantially the same) amount of force application may be repeated numerous times, thereby providing repeated same-force application to the face 14F, from which test measurements may be taken and analyzed with an expectation of a repeated same electrical response. Such responses, therefore, may provide a measure or indication of the ongoing fitness or operational characteristics of the pickup 14, or whether they have changed between repeated operations. Any material change (e.g., measure from standard deviation or the like) in subsequent measures, therefore, may represent either an environmental change or otherwise a change (e.g., degradation) in the performance of the pickup 14. Thus, if a sufficient change in the pickup 14 performance is so detected, this could signal the pickup 14 is timely for repair, refurbishment, or replacement. According, the computing system 30 may be readily programmed by one skilled in the art, given the teachings of this document, to store, analyze, report, and trigger indications in response to detections beyond thresholds or the like.

Continuing in FIG. 1B, after the mass 32 passes through the lower chamber 38 and contacts the face 14F (see FIG. 1A), the mass 32 advances though an exit port 40 to a lift chamber 42. In a preferred embodiment, the advancement of the mass 32 in this direction may be further facilitated by way of air injection, such as from an air puffer 44, that fluidly communicates air through an air channel 46 that is opposite the exit port 40. The air puff, therefore, further moves the mass 32 in the direction thus described.

Looking to FIG. 1C, once the mass 32 is located in the lift chamber 42, the lift chamber 42 is moved upward, relative to the lower chamber 38 and the upper chamber 34 as shown by a vertical arrow. In a preferred embodiment, this is achieved by having the lift chamber 42 concentrically and slidably positioned relative to the lower chamber 38 and the upper chamber 34, for example with an outer cylindrical member 16OCM about an inner cylindrical member 16ICM. Additionally, because the retaining member 36 extends generally away and horizontally from the inner chamber 34, then outer cylindrical member 16OCM preferably includes a slot or the like so that the outer cylindrical member 16OCM may move upward without being impinged, blocked, or otherwise prevented by the retaining member 36 from moving upward, relative to the inner chamber member 16ICM. Accordingly, as shown in FIG. 1C, once the outer chamber member 16OCM is moved to a position high enough relative to the inner chamber member 16ICM, the falling mass 32 is aligned with an upper chamber entry area 34EA, so that the force of gravity (and/or an incline along the bottom of the lift chamber 42) causes the mass 32 to move from the lift chamber 42, through the chamber entry area 34EA, into the upper chamber 34. Due to the conical shape of the upper chamber 34, the mass 32 continues to advance until again stopping atop the horizontal portion of the retaining member 36. Next, the outer cylindrical member 16OCM may be lowered back to the position shown in FIG. 1B, and with the falling mass 32 now positioned again as shown in FIG. 1A. Hence, the process is repeatable, whereby in each instance the falling mass may be dropped from the position of FIG. 1A, to the face 14F of the pickup 14, in a controlled and repeatable member as governed in part by the release of the retaining member 36 and the passage through lower chamber 38.

Given the preceding, a preferred embodiment includes a testing procedure and methodology associated with the use of the system 10. A preferred testing procedure for the inventive scope may include some or all of the following (but not necessarily in the sequence of ordering as shown below):

1. Power on computing system 30.
2. Position the pickup 14 into structure 12 (e.g., by threading), which thereby also brings the electrical interface (e.g., terminal(s)) of the pickup 14 into contact and communication with the circuit assembly 26 and the computing system 30.
3. Record (e.g., digitally, such as in a memory or other data storage device) detonation pickup serial number for later use.
4. Level the base 18, via the leveling feet 20, on a (e.g., bench) surface.
5. Thread the application member 16 onto detonation pickup 14 face threads.
6. Insert cabling (e.g., USB) into open port on the computing system 30.
7. Insert cabling (e.g., USB) into the port on the base 18.
8. Open a tester program located on the computing system 30.
9. Select the interface (e.g., Com Port) associated with the system 10 from a drop-down menu.
10. Place the mass 32 into the upper drop chamber 34.
11. Enter the detonation pickup serial number, as recorded from step 3.
12. Left click mouse button on the green "Start" button on application screen. User will have time period (e.g., 10 seconds) to pull the retaining member 36 to initiate a testing sequence.
13. Pull the retaining member 36 to initiate a test sequence by advancing the mass 32 to contact the pickup face 14F to create a response (which thereby releases the mass 32 to accelerate from gravity a fixed height within the drop chamber and strike the pickup face 14F, after which the mass 32 preferably advances (e.g., by air puffer) to the exit port 40, from where it may be removed/extracted/ejected from the test device and re-inserted from the top for subsequent testing).
14. Via the computing system 30, capture time varying impulse and/or ringing electrical responses to mass striking pickup face 14F.
15. Evaluate response(s) and display/convey test results of the test sequence, for example on a screen or other output or storage device.

This process (steps 10 to 15, or the entirety of steps 1-15 if the pickup 14 is put back into operation between tests) may be repeated, either close in time or after a longer period, if for example the device is tested in the configuration of FIG. 1A, then removed and used again with a test engine, then removed from the test engine and re-tested anew in the configuration of FIG. 1A.

In differing preferred embodiments, the step 15 captured response may be affected by various physical properties, such as the hardness, density, mass, volume, elasticity and coefficient of restitution, of the falling mass 32 (or, as shown below, fluid) acting upon the detonation pickup face 14F, which can create a wide array of time-varying impulse and ringing electrical responses. The inventive scope, therefore, permits subjecting the pickup to varying simulations of pickup facial forces. This allows preferred embodiment apparatus to record and measure varying simulated conditions affecting the pickup 14. Moreover, different preferred embodiments evaluate the response magnitude, or other attributes (e.g., shape, signature, decay, and the like), as representative of various magnetic and mechanical attributes and characteristics of the pickup 14. Examples of such pickup electrical, magnetic, and mechanical attributes and characteristics, as may be selectively or cumulatively analyzed by computing system 30 as part of various preferred embodiments, include:

1. Inductance
2. Capacitance
3. Load impedance
4. Electrical Resonant frequency
5. Mechanical Resonant frequency
6. Source impedance
7. Graphical representation of signal response
8. Peak signal response
9. Frequency of signal response
10. Integration of signal response
11. Differentiation of signal response
12. Charge time
13. Discharge time
14. Maximum Q (frequency sweep)
15. DC Resistance
16. Mechanical Attributes From the preceding, a preferred embodiment avails from, and the inventive scope recognizes, that electrical and mechanical characteristics of a detonation pickup 14 may be derived from a controlled force being applied to the pickup face 14F (or, alternatively, from electrical energy in the form of voltage or current being applied to the pickup's electrical terminals). Other attributes also are contemplated for invoking, capturing, and interpreting the signal response. For example, the applied test electrical energy may be steady state or alternating. An example of this would be to apply a frequency sweep to the pickup to determine a resonant frequency or to apply an oscillating signal to determine the pickup's impedance characteristics. Another example would be to apply electrical energy to the pickup to measure its resistance, inductance or capacitance. Preferred embodiments are envisioned to allow for the apparatus to be manually or non-manually functioned. This would allow for a basic manually operated apparatus or other embodiments of varying levels of automation, up to a fully automated and automatic testing apparatus. Examples of this may be found in embodiment variations that have automated actuation of the face striking mass placement, striking mass release along with other forms of actuation, and automation that would enhance the user's experience. In all events, and as discussed earlier, repeated measurements, close or far in time, at same or differing intervals, of pickup characteristics, in addition to, or other than DC resistance and in response to a predictable input force stimulus to the pickup face provide a robust apparatus and methodology for evaluating operability of the pickup.

Figure 2:
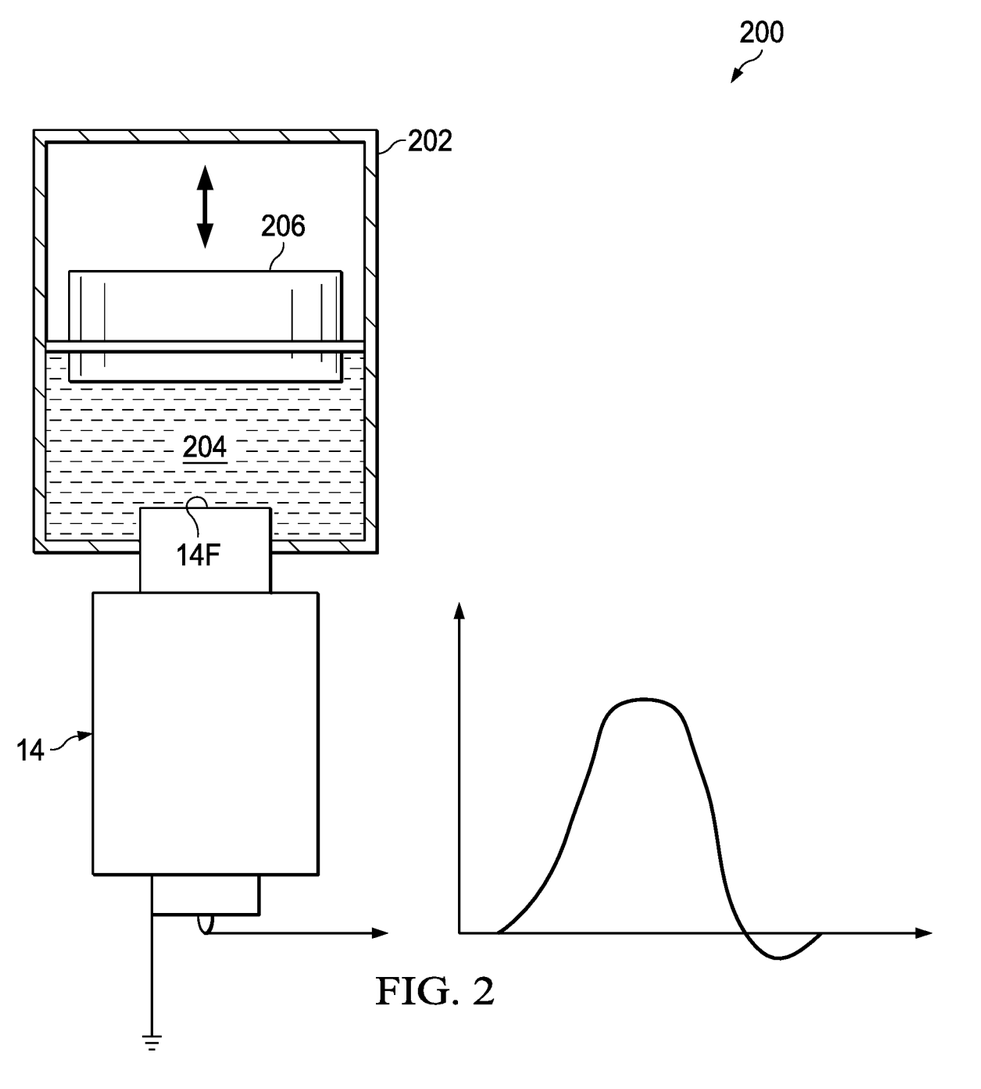
FIG. 2 illustrates an apparatus for applying a fluid (gas, liquid, plasma or mixture of) pressure force to the pickup face.

Another preferred embodiment is shown in FIG. 2, which illustrates an apparatus 200 for applying a fluid 204 (gas, liquid, plasma or mixture of) pressure force to the pickup face 14F. For example, a fluid chamber 202 may be used as the force application member 16 (see FIG. 1A), including for example the fluid 204 and an actuator apparatus (e.g., a piston 206) for advancing the fluid 204 to apply (or increase the pressure of) to the pickup face 14F. While not shown, it should be understood that the pickup 14 of apparatus 200 is likewise coupled to the electromechanical structure 12 of FIG. 1A, thereby likewise allowing repeated application of force to the face 14F, and capture and analyses of the responsive signals.

Figure 3:
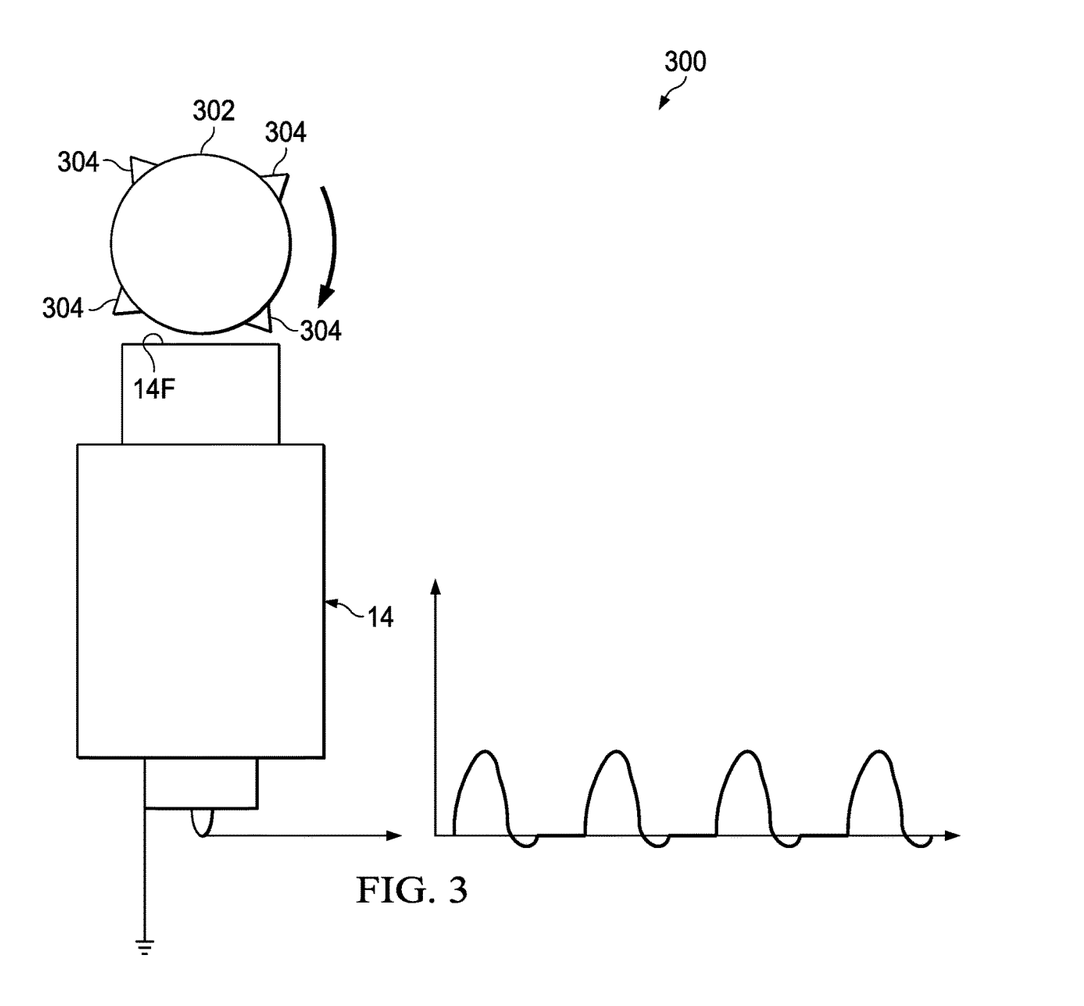
FIG. 3 illustrates an apparatus for applying a force, in response to a rotational member, to the pickup face.
Figure 4:
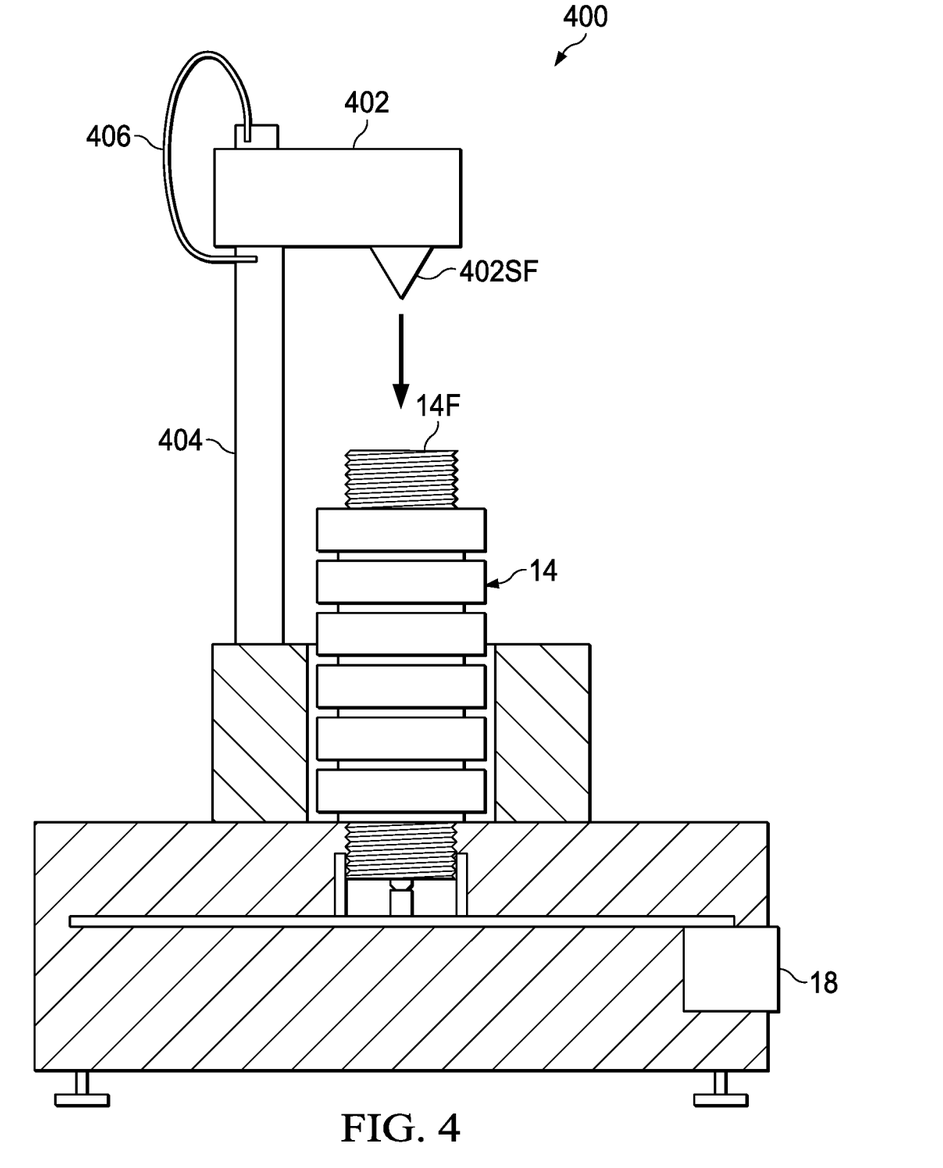
FIG. 4 illustrates an apparatus for applying a force, in response to a guided member, to the pickup face.

Another preferred embodiment is shown in FIG. 3, which illustrates an actuator apparatus 300 for applying a force, generated by a rotating wheel 302 with protrusions 304 (e.g., pads). In operation, the wheel 302 rotates (e.g., mechanically, or by operation of a motor (not shown)), whereby as the wheel 302 rotates, each protrusion 304 eventually makes physical contact with, as the rotational position of the protrusion 304 along the wheel approaches, and then contacts, the pickup face 14F, causing the pickup 14 to generate an electrical signal response. Again while not shown, it should be understood that the pickup 14 of apparatus 300 is coupled to the electromechanical structure 12 of FIG. 1A, thereby again allowing repeated application of force to the face 14F, and capture and analyses of the responsive signals, as described above Another preferred embodiment is shown in FIG. 4, which illustrates an actuator apparatus 400 for applying a force (from falling/sliding) to a face 14F of a detonation pickup 14. Apparatus 400 includes a sliding or guided mass 402 for striking the face 14F. More particularly, a guide 404 extends upward from the base 18 and supports the guided mass 402 above the face 14F. Upon actuation, such as by pulling a retaining member 406 (akin to the retaining member 36 in FIG. 1A), the mass 402 is released from its vertical position, and falls downward, guided by the guide 404 (and gravity), until a striking face 402SF of the falling mass 402 physically contacts the pickup face 14F. As with earlier embodiments, the striking action is repeatable, where in apparatus 400 this is achieved by lifting the falling mass 402 back into the position shown in FIG. 4, retaining it via the retaining member 406, and subsequently releasing it by a repeat actuation (e.g., pulling) of the retaining member 406. In each instance, therefore, the induced electrical signal of the pickup 14, in response to the force application of the falling mass 402, is captured and processed as described above.

Figure 5:
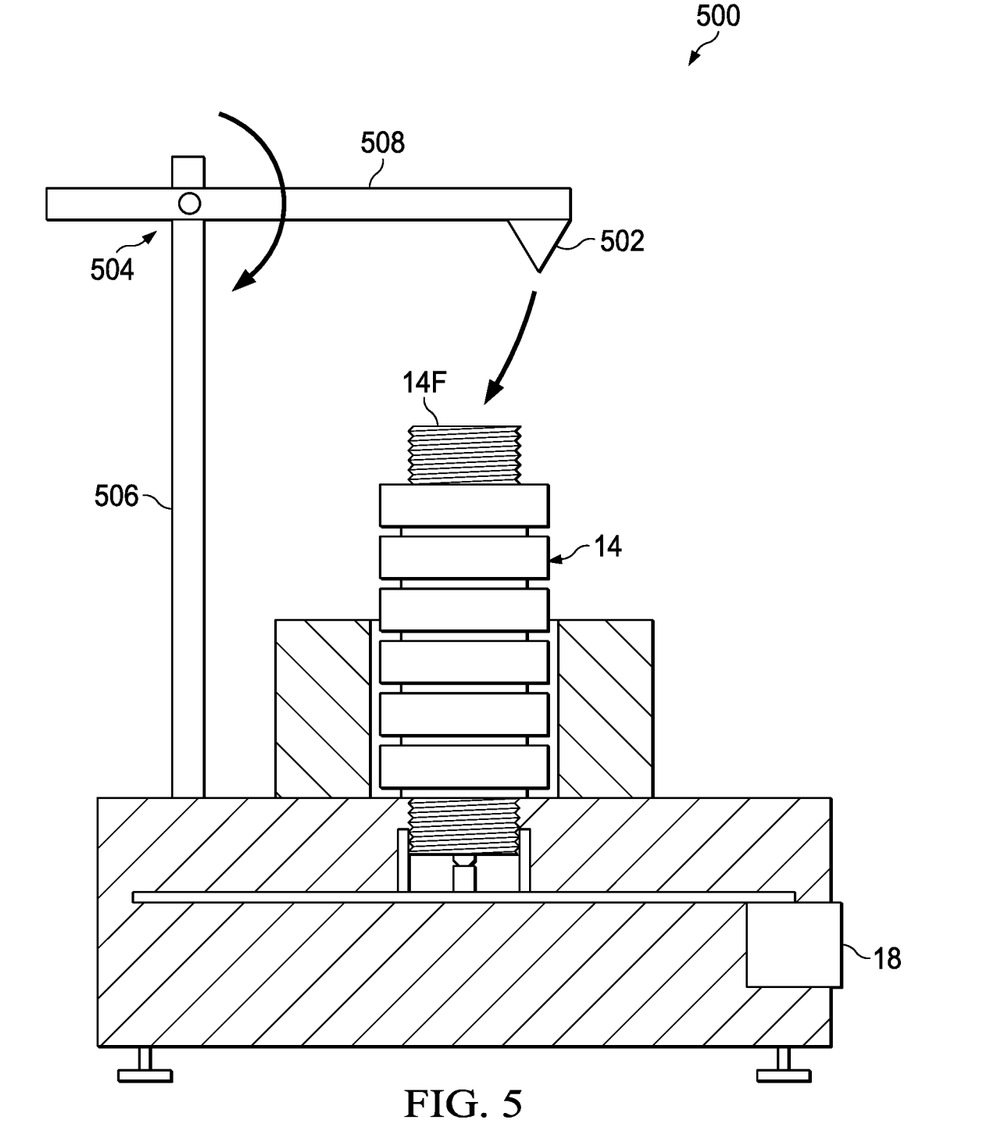
FIG. 5 illustrates an apparatus for applying a force, in response to a pivoting member, to the pickup face.

Another preferred embodiment is shown in FIG. 5, which illustrates an actuator apparatus 500 for applying a force (via a pivoting action) to a face 14F of a detonation pickup 14. Apparatus 500 includes a lever arm mass 502, pivoting about an axis 504, and operable to strike the pickup face 14F. The axis 504 is preferably defined by a supporting structure coupled to the base 18 and for retaining the lever arm mass 502 in an initial position (shown in FIG. 5), from which the mass 502 is released (e.g., by a pin or the like) to fall in an arcuate path and then strike the face 14F. In the example of FIG. 5, the supporting structure includes a first arm 506 between the base 18 and toward the axis 504, and a second arm 508 that pivots at or near one end about the axis 504 that supports the lever arm mass 502 at or near its other end. As with earlier embodiments, the striking action is repeatable, where in apparatus 500 this is achieved by lifting the lever arm mass 502 back into the position shown in FIG. 5, retaining it, and subsequently releasing it by a repeat actuation. In each instance, therefore, the induced electrical signal of the pickup 14, in response to the force application of the lever arm mass 502, is captured and processed as described above.

Figure 6A:
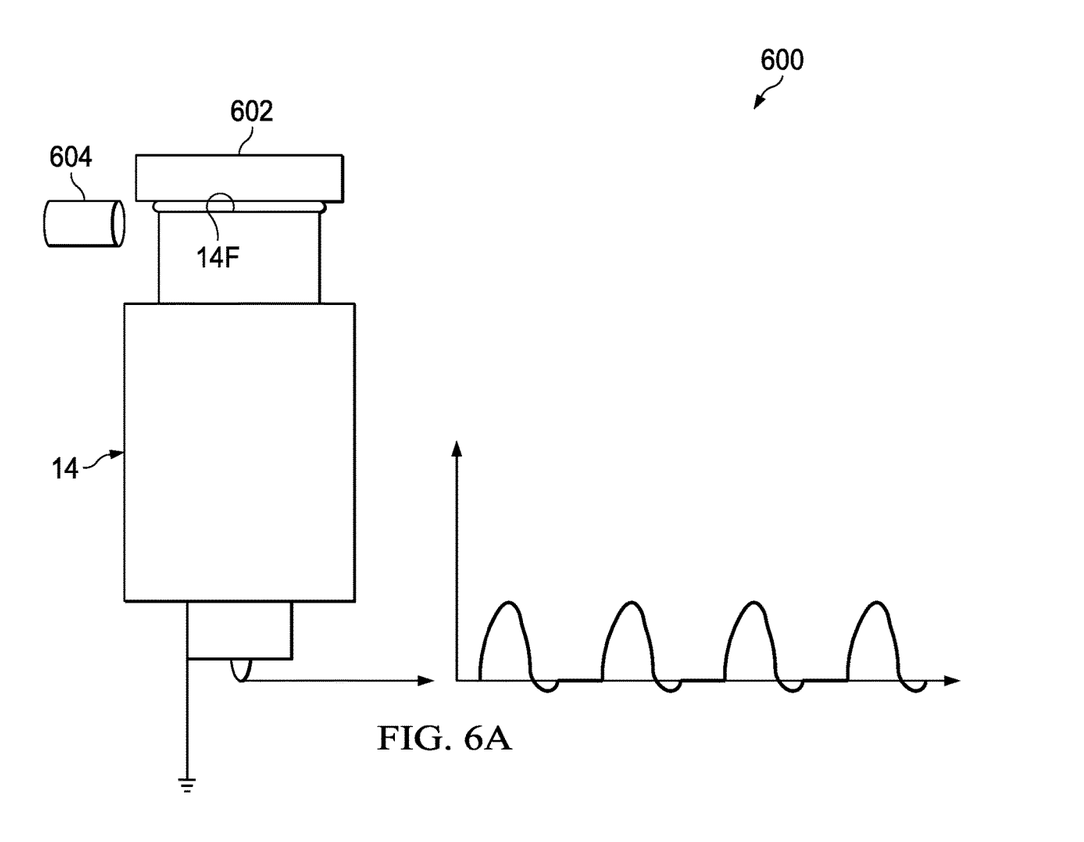
FIG. 6A illustrates an apparatus for applying a wave force along a physical medium to the pickup face.
Figure 6B:
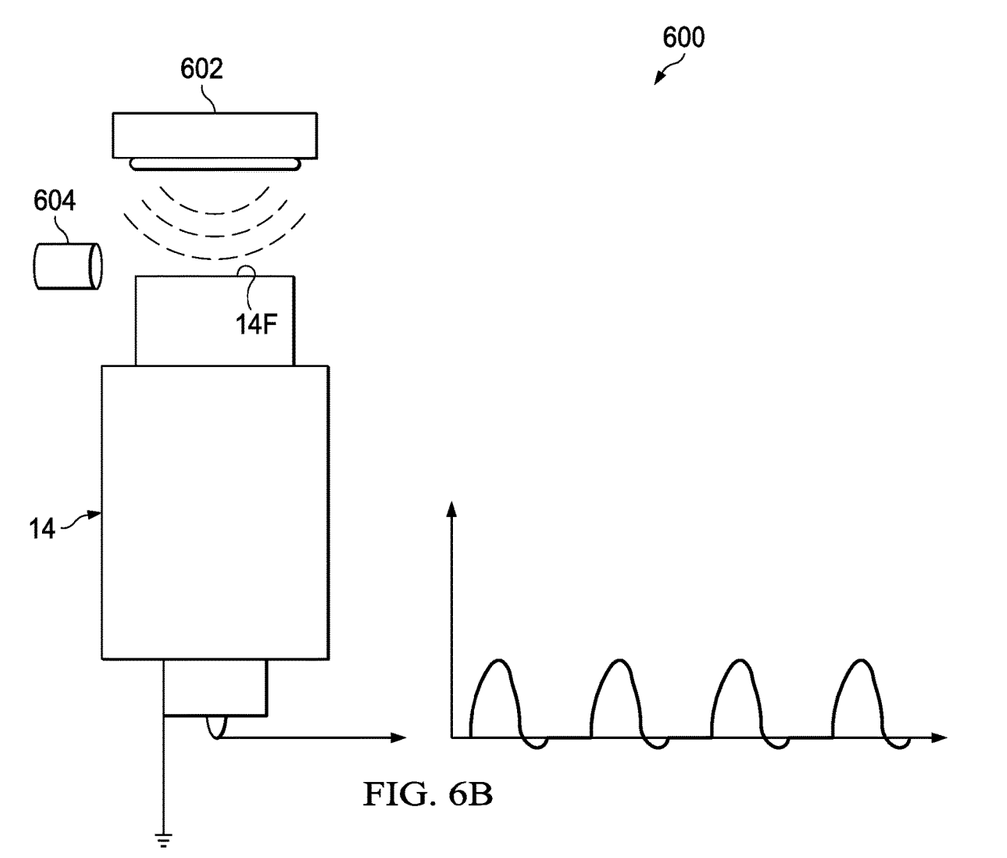
FIG. 6B illustrates an apparatus for applying a wave force, through the air, to the pickup face.

Another preferred embodiment is an apparatus 600 for applying a force to a detonation pickup by an electromechanical driver (e.g., transducer) 602 shown in FIG. 6A and FIG. 6B. FIG. 6A shows the use of the driver 602 in physical contact with the pickup face 14F, so the waves emitted by the driver 602 pass along a physical medium between the driver 602 and the face 14F. FIG. 6B shows the driver 602 exciting the pickup face 14F with waves 604 that pass in the air between the driver 602 and the face 14F. In either instance, the driver 602 is an actuator used to apply a force upon the face 14F by way of emitting a wave, and to induce an electrical signal response that is to be captured and processed as described previously. Each embodiment also would be capable of repetition to create a cyclic, repetitive, excitement of the face 14F. The value of these embodiments is to repetitively excite the detonation pickup 14 for a continuous time period in which the detonation pickup is excited for several thousand cycles, mimicking in some respects an actual engine running, without the added complexity and other issues from the use of an actual test engine. The excitement driver 602 is used to deliver an excitement event that will induce the detonation pickup 14 to create an output of a known, repeatable amplitude so as to test the detonation pickup's repeatability over time. An example of this would be to run the excitation driver for 5,000 events in a row with an excitement to excitement period of 200 milliseconds, mimicking a 600 RPM running engine. In a preferred embodiment, the detonation pickup's output signals created from the excitement events are captured and the peak values stored. The peak values are evaluated, for example with standard statistical mathematics to find the mean value and standard deviation of the 5,000 events. These basic statistical values in this preferred embodiment approach would be a quick reference for the operator to determine if the detonation pickup being tested has a repeatable and consistent output signal. This would help the operator to identify output signal bias characteristics of the detonation pickup.

The FIGS. 6A and 6B embodiments also may include, as shown, an audio microphone 604 to "listen" for the driver actuation as confirmation of the face excitement event. This may be an important feature for an automated test. In this manner, a test may be started by an operator and the testing could continue without continuous interaction/inspection from the operator, as the response of the microphone 604 can confirm that driver actuation is continuing, for example in the absence of the operator's presence. In other words, each time the driver 602 actuates, the microphone 604 is operable to capture a responsive signal to the actuation, and may be coupled to additional apparatus (e.g., computing system 30 of FIG. 1A) to confirm that for each actuation (or some number of actuations) that a microphone response is received. The operator may not, therefore, be required to continuously monitor the testing process of the continuous excitation events and may return to other needed activities, as any failure of the driver 602 to actuate would be detected in an absence of a respective response in the microphone 604. In this way, the microphone 604, in combination with computing system 30, provides an audio "listening" circuit which may add a great deal of secondary monitoring of the automated test. Thus, if the test is completed, and no response from the pickup was received, the audio microphone 604 responses will confirm the test was properly conducted, and the absence of a pickup response will answer an operator's question of "did the excitation driver event actually occur, as compared to, does the absence of a response indicate a faulty signal output of the detonation pickup"? This is an important question to be answered and this valued function can be achieved by the addition of the audio listening microphone 604 being used as an excitement event confirmation for comparison to the detonation pickup's output signals. An example of this type of feedback and confirmation may take the form of the excitement transducer being signaled to start an excitation event and then an audio "listening" channel is opened in which to monitor if there is an actual "thumping" sound generated by the excitation event driver. The output signal of the detonation pickup 14 that coincides with the excitation event is then captured. If the audio "listening" microphone 604 recorded an audible thumping sound, the excitation event would be considered an actual excitation event and the event would be confirmed. This would allow the operator to understand if the detonation pickup did not respond to an actual excitation event as to indicate a detonation pickup fault condition.

Figure 7:
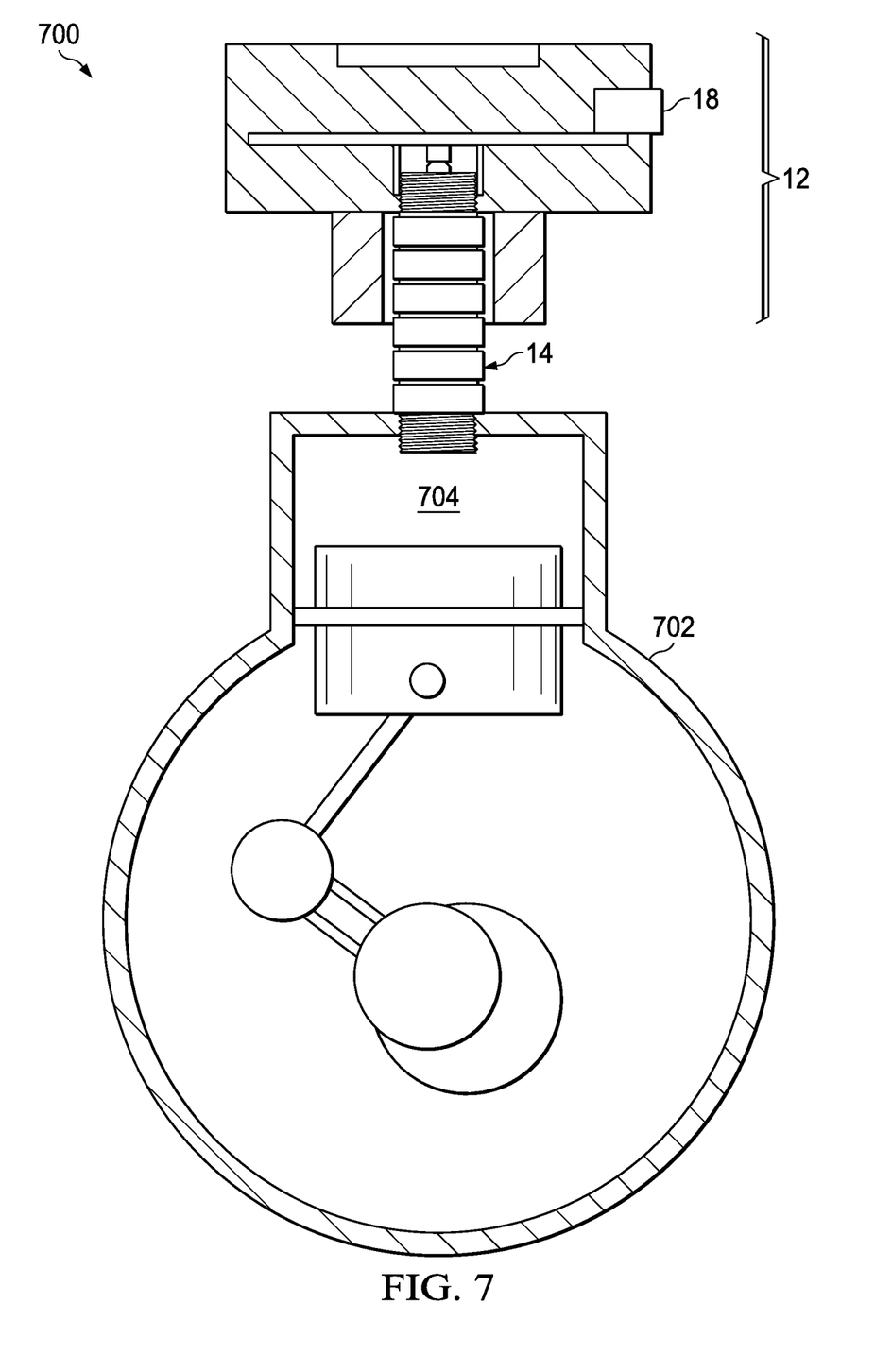
FIG. 7 illustrates a preferred embodiment electromechanical structure coupled to a pickup when the pickup is connected to a test engine.

FIG. 7 illustrates that the preferred embodiment the electromechanical structure 12 of FIG. 1A (and other Figures) also may be coupled to a pickup 14 directly when the pickup 14 is still affixed to a test engine 702, where the coupling of the pickup 14 to the test engine 702 is as known in the art (e.g., by threading the pickup in a combustion chamber). With the added apparatus of the preferred embodiment, however, signals from the detonation pickup 14 may be coupled, via the electromechanical structure 12 and its circuit assembly 26, to the computing system 30 (see FIG. 1A), while the test engine 702 is running. In this regard, notably the prior art only looks at the output signal of the detonation pickup at the time (or peak) of a detonation event, and an operator would initiate a diagnostic function if the detonation pickup's signal was erratic, noisy, or diminished in some form. The clear advancement of a preferred embodiment is that the detonation pickup 14 may be actively energized by signals applied to the terminal(s) 14T, via the computing system 30, rather than merely "listening" for inferior quality signals. Specifically, in this preferred embodiment apparatus and methodology, computing system 30 revaluates signals received from the pickup 14 and identifies "quiet" times, that is, times between the typical cycles of signals induced in the pickup 14 by the rotation of the test engine 702 and the normal combustion cycle in the combustion chamber 704 (e.g., as determined by the cyclical/periodic nature of the running test engine, including engine timing, crankshaft rotation, and the like). Thus, during these quiet times, that is periods away from the ordinary (timed) combustion/detonation events, the computing system 30 and/or the electrical interface 28 applies electrical energy on to the electrical terminals 14T of the detonation pickup 14. Also during these non-combustion quiet times, while no combustion event is occurring, the detonation pickup 14 may be excited by other sources, such as pressure variations within the combustion chamber 704, as well as vibrations caused by mechanical sources, such as connecting rod bearing slack take-up during the piston direction change points, along with other vibration sources such as those associated with intake and exhaust valve closing. These types of noise sources may induce an electrical signal from the detonation pickup 14. In any event, these additional realized responses, during these quiet time periods and in which a preferred embodiment delivers electrical energy to the electrical terminals 14T of the detonation pickup 14, are also preferably used from which diagnostic tests may be run, for example as pertaining to values as resistance, inductance, capacitance and impedance. A preferred embodiment further uses these test values to help determine the health, fit-for-use and precision bias detection and quantification, while the detonation pickup is operating in its intended use.

Given the preceding, one skilled in the art should appreciate that the preferred embodiments are intended to help reduce troubleshooting time and reduce measurement system biases, thereby resulting in reduced maintenance costs and increased profitability through increased measurement precision and improved diagnostics. The inventive scope, therefore, provides an enhanced diagnostic apparatus and system that also will help technicians to overcome the long and expensive learning curve of diagnosing the health and performance envelope of detonation pickups. Moreover, while various aspects have been described, still others are contemplated. For example:

the apparatus can be utilized in a static or dynamic system.

the apparatus may be portable or permanently installed.

the apparatus may be manually or non-manually actuated, adjusted, placed or cycled.

the apparatus may be utilized in one instance, continuously or periodically.

the apparatus may be temperature compensated or non-temperature compensated.

the apparatus may be self-powered or externally powered.

the system digital recordings may be stored in local memory or communicated for external memory storage.

information about the apparatus and testing data may be displayed locally or communicated to an external display device or system.

applied test electrical energy may be steady state or alternating in the form of voltage or current.

the apparatus may display the apparatus' normality to gravity or grade of level.

Thus, various other embodiments, advantages and features of the invention will become apparent to those skilled in the art from the accompanying disclosure and drawings.

What is claimed is:

1. A detonation pickup testing system, comprising:
apparatus for coupling to at least one terminal of a detonation pickup; and
a computational system, for communicating with the pickup via the apparatus, to test at least one characteristic of the detonation pickup, the at least one characteristic excluding or in addition to DC resistance of the detonation pickup.

2. The system of claim 1 and further comprising apparatus for applying a force corresponding to an event other than an engine combustion event, upon a detonation pickup face of the detonation pickup.

3. The system of claim 2 wherein the apparatus for applying a force is for applying a force comprising at least one of a fluid force, a physical contact force, or a wave force.

4. The system of claim 2 wherein the apparatus for applying a force comprises apparatus for applying a force by controllably advancing a mass to contact a face of the detonation pickup.

5. The system of claim 2 wherein the apparatus for applying a force comprises apparatus for applying a force by rotating a mass to contact a face of the detonation pickup.

6. The system of claim 2 wherein the apparatus for applying a force comprises apparatus for applying a force by increasing a fluid pressure against a face of the detonation pickup.

7. The system of claim 2 wherein the apparatus for applying a force comprises a transducer for communicating a wave toward a face of the detonation pickup.

8. The system of claim 7 wherein the transducer is physically coupled to the face of the detonation pickup.

9. The system of claim 7 wherein the transducer is separated by an air gap from the face of the detonation pickup.

10. The system of claim 7 and further comprising a microphone for capturing an audio signal in response to a wave being emitted by the transducer.

11. The system of claim 1 wherein the computational system is for causing an electrical stimulus to be applied, via the apparatus, to the at least one terminal.

12. The system of claim 1 wherein the at least one characteristic comprises at least one of an electrical or magnetic property of the detonation pickup.

13. The system of claim 1:
wherein the apparatus for coupling is coupled to the at least one terminal during a time when the pickup is affixed to a combustion engine having a combustion cycle during which a combustion event occurs; and
wherein the computational system is to test the at least one characteristic during a period that the combustion engine is operating, the period other than during the combustion event.

14. The system of claim 1:
wherein the at least one characteristic comprises a magnetic property of the detonation pickup; and
wherein the apparatus for applying a force comprises apparatus for applying a force by increasing a fluid pressure against a face of the detonation pickup.

15. The system of claim 1, wherein the computational system is for communicating with the pickup via the apparatus, to test at least one characteristic in response to an event other than an engine combustion event.

16. An apparatus used to test a detonation pickup, the detonation pickup for testing ignition properties of fuel, comprising:
a member for coupling to the pickup; and
apparatus, coupled to the member, for retaining a movable device relative to the member, the apparatus for retaining comprising apparatus for retaining the movable member at a first position away from a face of the pickup and apparatus for releasing the apparatus for retaining so as to apply an increase in force against the face.

17. The apparatus of claim 16 wherein the movable member comprises a falling mass.

18. The apparatus of claim 16 wherein the movable member comprises a member for compressing a fluid force against the face.

19. The apparatus of claim 16 wherein the movable member comprises a rotating mass with a surface for selectively contacting the face in response to rotation of the rotating mass.

20. An apparatus used to a test a detonation pickup that is used for testing ignition properties of fuel, comprising:
a test engine for coupling to a detonation pickup; and
a member for coupling electrical energy stimulus to the detonation pickup while the test engine is running and during a period of time separated from a combustion event of the test engine.

21. The apparatus of claim 20 and further comprising apparatus for measuring a response from the detonation pickup during the period of time separated from a combustion event of the test engine.

22. An apparatus used to test a detonation pickup, the detonation pickup for testing ignition properties of fuel, comprising:
a member for coupling proximate a face of the pickup; and
an actuator, coupled to the member, for controlling a force applied to the face of the pickup, the force representative of an event other than an engine combustion force event.

23. The apparatus of claim 22 wherein the actuator is for applying a force comprising at least one of a fluid force, a physical contact force, or a wave force.

* * * * *